United States Patent [19]

Cristol et al.

[11] Patent Number: 4,574,074

[45] Date of Patent: Mar. 4, 1986

[54] PROCESS FOR THE PRODUCTION OF ALUMINUM TRIHYDROXIDE HAVING A MEDIUM OF LESS THAN 4 MICRONS, WHICH CAN BE VARIED AS REQUIRED

[75] Inventors: Benoit Cristol; Jacques Mordini, both of Provence, France

[73] Assignee: Aluminum Pechiney, Gardanne, France

[21] Appl. No.: 622,083

[22] PCT Filed: Oct. 18, 1983

[86] PCT No.: PCT/FR83/00210

§ 371 Date: Jun. 13, 1984

§ 102(e) Date: Jun. 13, 1984

[87] PCT Pub. No.: WO84/01569

PCT Pub. Date: Apr. 26, 1984

[30] Foreign Application Priority Data

Oct. 20, 1982 [FR] France .................................. 82 17955

[51] Int. Cl.$^4$ .................................................. C01F 7/02
[52] U.S. Cl. ..................................... 423/124; 423/127; 423/629; 423/121; 23/301; 23/305 A
[58] Field of Search ............... 423/127, 629, 121, 124; 23/301, 305 A

[56] References Cited

U.S. PATENT DOCUMENTS 3,838,980 10/1974 Gnyra ................................. 423/119
4,150,952 4/1979 Lafleur et al. ...................... 423/121

FOREIGN PATENT DOCUMENTS 540517 5/1957 Canada ................................. 75/119

Primary Examiner—Herbert T. Carter
Attorney, Agent, or Firm—McDougall, Hersh & Scott

[57] ABSTRACT

A process for the production of aluminum trihydroxide having a controlled median diameter of less than 4 microns, with a unimodal distribution and minimum deviation. The process comprises grinding aluminum trihydroxide until the aluminum trihydroxide has a specific BET surface area of at least 8 m$^2$/g, adding the ground aluminum trihydroxide to a sodium aluminate solution, and then decomposing the solution to precipitate aluminum trihydroxide having the required median diameter.

14 Claims, No Drawings

PROCESS FOR THE PRODUCTION OF ALUMINUM TRIHYDROXIDE HAVING A MEDIUM OF LESS THAN 4 MICRONS, WHICH CAN BE VARIED AS REQUIRED

This invention relates to a process for the production of aluminium trihydroxide having a median diameter which can be varied as required of less than 4 microns, having a unimodal distribution and minimum deviation. The aluminium trihydroxide is produced by the decomposition of a hot supersaturated solution of sodium aluminate in the presence of ground aluminium trihydroxide having a specific surface, measured according to the B.E.T. method, of at least equal to 8 square meters per gram.

It is well established in the art to carry out the precipitation of aluminium trihydroxide from a supersaturated solution of sodium aluminate by the addition of a primer consisting of previously crystallised aluminium trihydroxide. The spontaneous generation of seed crystals in a solution of this type has been found to be extremely slow and difficult to produce and even non-existent, depending on the conditions of termperature and concentration of the treated medium.

For this reasons it is common practice in the Bayer process to favour the precipitation of aluminium trihydroxide from supersaturated sodium aluminate solutions resulting from the alkaline attack of aluminous ores due to the recycling of a considerable in a previous cycle.

However, such as it is carried out, this priming process results not only in the recycling of a very considerable quantity of previously precipitated aluminium trihydroxide, but above all in the production of grains of aluminium trihydroxide of an eminently variable size. The median dimensions and the deviation about this value are difficult to control, due to the fact that the dimensions of the grains of aluminium trihydroxide increase during the consecutive cycles and cause the formation of new seeds in a periodic rhythm.

However, those skilled in the art would like to be able to produce, for particular uses, aluminium trihydroxide, the median diameter of the precipitated particles of which is less than 4 microns, and the granulometry of which deviates only slightly about the desired median dimensions.

In fact, certain uses of aluminium trihydroxide require a granulometry, which is specific to them. In particular for uses such as fireproofing charges for synthetic polymers, gentle abrasives in cosmetology and charges used in the paper industry.

By the number of publications issued in this field, the specialized literature reveals the importance and the complexity of the research carried out by those skilled in the art to try to provide industrially viable solutions to the above-mentioned problems, and to control the size of the particles of aluminium trihydroxide.

Among the numerous solutions which have been proposed, some lead to the use of mechanical means and others, which are more numerous, lead to processes which use the resources of chemistry.

The first group which uses mechanical means concerns the production of aluminium trihydroxide, the median diameter of which is generally from 1 to 30 microns, by grinding a coarse aluminium trihydroxide which is obtained according to the Bayer process. A process of this type is described in French Pat. No. 2,298,510 which claims the production of an aluminium hydroxide intended for use in cosmetology, the mean diameter of which is from 1 to 25 microns, by grinding a coarse hydroxide in the presence of an organic acid. Such process can be used in the production of an aluminium hydroxide having a mean diameter of more than 15 microns, because it remains reasonable in terms of energy consumption and technological investment. However, if an aluminium hydroxide is to be produced which has a much smaller mean diameter, such as less than 4 microns, the use of such a means is extremely costly, because the mean diameter which is desired demands a considerable energy consumption and the use of a very high grinding capacity which is unacceptable within the scope of an industrial production.

The second group which uses chemical resources proposes processes pursuing the aim of obtaining an aluminium trihydroxide having a regulated granulometry and comprising carrying out the decomposition of supersaturated sodium aluminate solutions in the presence of very fine aluminium trihydroxide which performs the function of a primer.

A first process which has several stages and is described in French Pat. No. 1,290,582 initially comprises preparing the priming material consisting of aluminium trihydroxide having very fine and regular grains, then using this priming material for the decomposition, in successive stages, of a supersaturated solution of sodium aluminate. The priming material is prepared by the sudden and violent dilution of a strongly concentrated sodium aluminate solution, having a molecular ratio of $Na_2O:Al_2O_3$ as close as possible to unity, thus causing a marked supersaturation of the aluminium trihydroxide which separates in the form of a gel. This gel is formed from spherules swollen with water, containing numerous microscopic seeds of aluminium hydroxide having a mean diameter of from 0.3 to 0.5 microns.

When the priming material having very small grains has been prepared, it is presented as an aqueous suspension in its mother solution, into which the supersaturated aqueous solution of sodium aluminate to be decomposed is introduced in stages; each introduction stage being followed by several hours of agitation. This agitation is continued after the final introduction of the solution to be decomposed, until decomposition is complete.

Another process which is disclosed by French Pat. No. 2,041,750 initially comprises producing a very fine aluminium trihydroxide by carbonation of a sodium aluminate solution, under a controlled temperature, by causing the formation of a gel and the conversion of this alumina gel into a stable crystalline phase by producing a suspension of this gel in a supersaturated solution of sodium aluminate maintained under agitation. If the granulometry of the resulting aluminium trihydroxide is too small, said aluminium trihydroxide may be used as a primer for the preparation of an aluminium trihydroxide having the desired granulometry by decomposition of a supersaturated sodium aluminate solution.

Moreover, an older process which is described in U.S. Pat. No. 2,549,549 proposes the introduction of an aluminium salt into a sodium aluminate solution originating from the Bayer process, thus producing an alumina gel, then the conversion of some of this gel into crystalline aluminium trihydroxide, and finally the introduction of the mixture thus obtained into a supersaturated solution of sodium aluminate which is to be decomposed and is maintained under agitation, thus causing the precipitation of the very fine aluminium trihydroxide.

Finally, through the various known publications which use chemical resources, it appears that the processes which are proposed for attempting to produce an aluminium trihydroxide having a very small median diameter by precipitation from a hot supersaturated solution of sodium aluminate involve the preparation of an alumina gel and its conversion a stable crystalline phase. However, those skilled in the art must note that the proposed processes provide incomplete and unsatisfactory solutions, because they lead to the production of particles of aluminium trihydroxide, whose size is inadequately controlled, due to the poor reproducibility of the gel quality and to the low stability of the gel in the time.

For this reason, based on the above-mentioned disadvantages, in continuing our research, we have found and perfected a process for the production of aluminium trihydroxide having a median diameter which can be varied as required and is less than 4 microns, having a unimodal distribution and a minimum deviation, by the hot decomposition of a supersaturated solution of sodium aluminate in the presence of primer. This process does not suffer from the above-mentioned disadvantages.

Accordingly, the present invention provides for the production of aluminium trihydroxide having a median diameter which can be varied as required and being less than 4 microns, is characterized in that in a first stage, aluminium trihydroxide is subjected to grinding until a ground aluminium trihydroxide is produced which has a specific BET surface area formed by the grinding operation which is at least equal to eight square meter per gram, then, in a second stage, the ground aluminium trihydroxide is brought into contact with all of a hot solution of sodium aluminate to be decomposed in a quantity such that the complete surface of said aluminium trihydroxide introduced in ground form is at least 100 square meters per liter of the supersaturated solution of sodium aluminate, and said solution is decomposed by subjecting the suspension which has formed to agitation until a weight ratio of dissolved $Al_2O_3$:caustic $NaO_2$ is obtained which is at the most equal to 0.7.

To facilitate the subsequent description of the present invention, it is necessary to recall that the concentration of caustic $Na_2O$ in grams per liter of the sodium aluminate solution expresses, as is well known, the total quantity of $Na_2O$ which is present in said solution in the bound form of sodium aluminate and in the free form of sodium hydroxide.

During our research, and in an attempt to improve the processes proposed by the prior art recommending the use of alumina gel, we attempted to substitute previously ground aluminium trihydroxide for said gel. We then observed with great interest that the introduction of this ground aluminium trihydroxide into a supersaturated solution of sodium aluminate entrained the precipitation of an aluminium trihydroxide, the median diameter of which was clearly smaller than the median diameter of the ground aluminium trihydroxide which we had introduced, whereas, according to our knowledge of the prior art, we were expecting an increase in the median diameter. From then on, continuing further in our research, we wished to verify the extent of this observation and, in order to do this, in new experiments, we substituted for the ground aluminium trihydroxide a precipitated aluminium trihydroxide having the same median diameter and having an almost identical distribution. We then found that, in the latter case, there resulted a considerable increase in the median diameter of the aluminium trihydroxide which was precipitating, as in the prior art processes.

Thus, we were able to state that the use of a ground aluminium trihydroxide in the decomposition of a supersaturated solution of sodium aluminate resulted in a very different behaviour compared to that of a non-ground aluminium trihydroxide of the same granulometry.

In order to gain a better comprehension of the parameters playing a part in the present process, we completed our research with the objective of controlling the conditions which are most favourable for the production of an aluminium trihydroxide which has a restricted granulometry and a median diameter of less than 4 microns.

The specific BET surface area which is formed by the grinding operation is given by the difference between the specific surface area of the ground aluminium trihydroxide and the specific surface area of the aluminium trihydroxide before it is subjected to the grinding operation. As already expressed, the specific BET surface area which results during grinding of the aluminium trihydroxide must be at least equal to 8 square meters per gram. It is generally from 10 to 25 $m^2$ per gram and preferably from 12 to 20 $m^2$ per gram.

The grinding operation of the aluminium trihydroxide which is carried out using any apparatus known to those skilled in the art may be carried out dry, but it may be desirable to carry out this operation in a liquid medium. In the latter case, the liquid phase which is used to suspend the trihydroxide is an aqueous medium which may be water.

The supersaturated solution of sodium aluminate which is treated according to the process of this invention generally results from the hot alkaline attack of an aluminous ore, such as bauxite, according to the Bayer process which is described in detail in the specialized literature and is well known to those skilled in the art. However, this solution may also be of a synthetic origin. Whatever its origin, the supersaturated solution of sodium aluminate generally has a concentration of caustic $Na_2O$ of from 50 to 200 grams, and preferably from 90 to 170 grams of $Na_2O$ per liter of sodium aluminate solution to be decomposed.

Moreover, it is desirable for this supersaturated solution of sodium aluminate to have a ratio by weight of dissolved $Al_2O_3$:caustic $Na_2O$ of from 0.8 to 1.3, but preferably from 1.0 to 1.2.

In addition thereto, the quantity of aluminium trihydroxide which is ground according to techniques known to those skilled in the art and which is introduced into the supersaturated solution of sodium aluminate to be decomposed is such that the total surface of the aluminium trihydroxide which is ground and introduced into the said solution is from 100 to 600 $m^2$ per liter and preferably from 200 to 400 $m^2$ per liter of supersaturated sodium aluminate solution.

When the ground aluminium trihydroxide is introduced in an adequate quantity into the hot supersaturated solution of sodium aluminate to be decomposed, the suspension which is thus produced is agitated and maintained in this condition for a time such that the weight ratio of dissolved $Al_2O_3$:caustic $Na_2O$ is at the most equal to 0.7.

This decomposition takes place in a medium which is subjected to agitation and is generally continued until a weight ratio of dissolved $Al_2O_3$:caustic $Na_2O$ of from 0.65 to 0.35, preferably from 0.60 to 0.40 is attained.

The decomposition of the supersaturated sodium aluminate solution in the presence of the ground aluminium trihydroxide takes place at a temperature of from 30° to 80° C. and preferably from 40° to 60° C.

Thus, the decomposition of the supersaturated sodium aluminate solution, during the second stage of the present process in the presence of the ground aluminium trihydroxide resulting from the first stage leads, at the end of these two stages, to the precipitation of aluminium trihydroxide having the desired median diameter of less than 4 microns and having a restricted granulometry.

The essential characteristics of the present invention will be better comprehended by reading the description of the following examples.

EXAMPLE 1

This example illustrates the possibility of producing on demand, according to the present process, aluminium trihydroxide having a median diameter of less than 4 microns and having a restricted granulometry.

To this end, and in the first stage of the present process, industrial aluminium trihydroxide is taken, resulting from the alkaline attack of a bauxite according to the Bayer process. Then, to carry out the grinding operation, an aqueous suspension of said aluminium trihydroxide at a concentration of 100 grams per liter of dry material is produced.

Grinding is carried out using a known type of apparatus, consisting of a cylinder having a horizontal rotational axis, of a useful diameter of 100 mm, the grinding support of which being formed by steel balls. 1 liter of the above-mentioned suspension is thus subjected to grinding using 2 kilos of balls having a diameter of 9 mm and 1 kilo of balls having a diameter of 6 mm.

After grinding for 24 hours, there resulted ground particles of aluminium trihydroxide having a BET surface of 13.5 $m^2$ per gram, measured according to the method described in the AFNOR X 11-621 and X 11-622 standards, whereas the aluminium trihydroxide had a BET surface before grinding of 0.10 $m^2$ per gram.

Later on, and to carry out the second stage of the present process, a supersaturated solution of sodium aluminate was used from the Bayer process which had the following composition:

| | |
|---|---|
| $Al_2O_3$ | 100 g/l |
| Caustic $Na_2O$ | 100 g/l |
| weight ratio of dissolved $Al_2O_3$ to caustic $Na_2O$ | 1 |
| Carbonated $Na_2O$ | 9 g/l |
| Organic C | 4 g/l |
| Cl | 6 g/l |

2 liters of the said solution and 30 g of ground aluminium trihydroxide (in the form of a suspension in water) are then introduced into a suitable reactor such that there are 15 g of ground aluminium trihydroxide per liter of supersaturated sodium aluminate solution to be decomposed.

The suspension thus produced is agitated by means of an agitator having a vertical axis with wide blades rotating at 60 r.p.m. The temperature of the suspension is maintained at 50° C. during the decomposition operation which lasted for 20 hours.

After decomposition, the ratio by weight of dissolved $Al_2O_3$:caustic $Na_2O$ was 0.4, thus indicating that 60% of the alumina in solution had precipitated.

The aluminium trihydroxide which was recovered at the end of this second stage had a median diameter of 2.1 microns, measured by the sedimentation method described in the AFNOR X 11-683 standard. Moreover, this aluminium trihydroxide had a very restricted granulometry, since 90% of the particules had a diameter of less than 3 microns and 90% of the particles had a diameter of greater than 1.5 microns.

By way of comparison, the same supersaturated solution of sodium aluminate was treated with a ground aluminium trihydroxide having a BET specific surface, formed by grinding, of only 4 $m^2$ per gram. By using the same apparatus and carrying out the same procedure as before, i.e., the same quantities of ground aluminium trihydroxide and supersaturated sodium aluminate solution to be decomposed, the same temperature, agitation speed and treatment time, a precipitated aluminium trihydroxide was obtained, the particles of which had a median diameter of 2 microns, but 10% of which had a diameter of greater than 10 microns.

EXAMPLE 2

This example illustrates the possibility of producing on demand, according to the process of the present invention, aluminium trihydroxide having a median diameter of less than 1 micron and having a restricted granulometry.

In the first stage of the present process, aluminium trihydroxide, precipitated from the Bayer process and having a BET specific surface of 2 $m^2$ per gram was subjected to a grinding operation in the same apparatus as the one used in Example 1.

To this end, an aqueous suspension of this aluminium trihydroxide was produced at a concentration of 100 grams per liter of dry material. Apart from the grinding time which was 30 hours, all the other conditions were identical to those of Example 1.

After grinding, ground particles of aluminium trihydroxide were obtained having a BET specific surface of 18 $m^2$ per gram.

Later on, and to carry out the second stage of the present process, a supersaturated solution of sodium aluminate was used from the Bayer process which had the following composition:

| | |
|---|---|
| $Al_2O_3$ | 110 g/l |
| Caustic $Na_2O$ | 100 g/l |
| Weight ratio of dissolved $Al_2O_3$ to caustic $Na_2O$ | 1.10 |
| Carbonated $Na_2O$ | 9 g/l |
| Organic C | 4 g/l |
| Cl | 6 g/l |

2 liters of the said solution and 40 g of ground aluminium trihydroxide (in the form a suspension in water) were then introduced into a suitable reactor such that there were 20 g of ground aluminium trihydroxide per liter of supersaturated sodium aluminate solution to be decomposed. The suspension thus produced was agitated by means of an agitator having a vertical axis and wide blades rotating at 60 r.p.m. The temperature of the suspension was maintained at 40° C. during the decomposition operation which lasted for 20 hours.

After decomposition, the weight ratio of dissolved $Al_2O_3$:caustic $Na_2O$ was 0.35, thus indicating that 68% of the alumina in solution had precipitated.

The aluminium trihydroxide recovered at the end of this second stage had a median diameter of 0.7 microns, and a granulometric analysis of the precipitated particles is as follows, in percentage of particles passing for each diameter given in microns.

| DIAMETER GIVEN IN MICRONS | % OF PARTICLES PASSING TO |
|---|---|
| 1.5 | 95 |
| 1.0 | 80 |
| 0.7 | 50 |
| 0.45 | 20 |
| 0.30 | 5 |

Thus, according to the process of the present invention, it is possible to produce an aluminium trihydroxide having a median diameter of less than 1 micron, and having a low granulometric dispersion.

We claim:

1. In a process for the production of aluminum trihydroxide by decomposing a supersaturated sodium aluminate solution by adding aluminum trihydroxide primer to said sodium aluminate solution and said solution is agitated to precipitate aluminum trihydroxide, the improvement comprising grinding the aluminum trihydroxide primer until said primer has a specific B.E.T. surface area of at least 8 square meters per gram, adding said primer to a hot supersaturated sodium aluminate solution at a temperature of from 30°–80° C. in a quantity up to 20 grams per liter of said solution such that the total surface area of said primer added is at least 100 square meters per liter of sodium aluminate solution, and then agitating the resulting suspension until a weight ratio of dissolved $Al_2O_3$ to caustic $Na_2O$ of at most 0.7 is obtained, whereby aluminum trihydroxide having a median diameter of less than 4 microns, with unimodal distribution and minimum deviation is precipitated.

2. A process for the production of aluminum trihydroxide according to claim 1 wherein the specific B.E.T. surface area formed by grinding is from 10 to 25 $M^2/g$.

3. A process for the production of aluminum trihydroxide according to claim 1 wherein the grinding operation of the aluminum trihydroxide is carried out dry.

4. A process for the production of aluminum trihydroxide according to claim 1 wherein the grinding operation of the aluminum trihydroxide is carried out in the suspension in an aqueous medium.

5. A process for the production of aluminum trihydroxide according to claim 1 wherein the hot supersaturated solution of sodium aluminate has a concentration of caustic $Na_2O$ of from 50 to 200 g/l.

6. A process for the production of aluminum trihydroxide according to claim 1 wherein the supersaturated solution of sodium aluminate has a ratio by weight of dissolved $Al_2O_3$:caustic $Na_2O$ of from 0.8 to 1.3.

7. A process for the production of aluminum trihydroxide according to claim 1 wherein the quantity of ground aluminum hydroxide primer which is used for the decomposition of the supersaturated solution of sodium aluminate is such the complete surface area of the aluminum trihydroxide which is ground and introduced into said solution is from 100 to 600 $m^2$ per liter of supersaturated sodium aluminate solution.

8. A process for the production of aluminum trihydroxide according to claim 1 wherein the suspension resulting from the addition of aluminum trihydroxide to the sodium aluminate solution is agitated until a ratio by weight of dissolved $Al_2O_3$:caustic $Na_2O$ of from 0.65 to 0.35, is attained.

9. A process for the production of aluminum trihydroxide according to claim 1 wherein the decomposition of the supersaturated sodium aluminate solution is carried out at a temperature of from 40° to 60° C.

10. A process for the production of aluminum trihydroxide according to claim 1 wherein the specific B.E.T. surface area formed by grinding is from 12 to 20 $M^2/g$.

11. A process for the production of aluminum trihydroxide according to claim 1 wherein the hot supersaturated solution of sodium aluminate has a concentration of caustic $Na_2O$ of from 90 to 170 g/l.

12. A process for the production of aluminum trihydroxide according to claim 1 wherein the supersaturated solution of sodium aluminate has a ratio by weight of dissolved $Al_2O_3$:caustic $Na_2O$ of from 1.0 to 1.2.

13. A process for the production of aluminum trihydroxide according to claim 1 wherein the quantity of ground aluminum hydroxide primer which is used for the decomposition of the supersaturated solution of sodium aluminate is such that the complete surface area of the aluminium trihydroxide which is ground and introduced into said solution is from 200 to 400 $M^2$ per liter of supersaturated sodium aluminate solution.

14. A process for the production of aluminum trihydroxide according to claim 1 wherein the suspension resulting from the addition of aluminum trihydroxide primer to the sodium aluminate solution is agitated until a ratio by weight of dissolved $Al_2O_3$:caustic $Na_2O$ of from 0.60 to 0.40 is attained.

* * * * *